United States Patent [19]
Brouwer

[11] Patent Number: 5,965,749
[45] Date of Patent: Oct. 12, 1999

[54] PROCESS FOR SYNTHESIZING SUBSTITUTED 2-BENZO [B] THIOPHENECARBOXYLIC ACIDS AND SALTS THEREOF

[75] Inventor: Walter Gerhard Brouwer, Guelph, Canada

[73] Assignees: Uniroyal Chemical Company, Inc., Middlebury, Conn.; Uniroyal Chemical Co./CIE., Elmira, Canada

[21] Appl. No.: 09/039,769

[22] Filed: Mar. 16, 1998

[51] Int. Cl.$^6$ .................................................. C07D 330/70
[52] U.S. Cl. .................................................. 549/57
[58] Field of Search ................................. 549/57

[56] References Cited

U.S. PATENT DOCUMENTS

| | | | |
|---|---|---|---|
| 5,298,630 | 3/1994 | Kagano | 549/57 |
| 5,777,110 | 7/1998 | Davis | 544/2 |

FOREIGN PATENT DOCUMENTS

| | | | |
|---|---|---|---|
| 5194484 | 8/1993 | Japan . | |

OTHER PUBLICATIONS

Rahman et al, J. Chem. Soc. Perkin Trans. I, pp. 385–390, 1984.

Kolasa et al, "Practical Synthesis of 2–Acetylbenz (b)thiophene", Syn. Comm. 23(6): 743–748 (1993).

Zambias et al, "The Synthesis of 5–Hydroxy–2,3–dihydrobenzob)thiophene (1) Via an Efficient One Step Preparation of 5–Nitro–Benzo(b)thiophene–2–Carboxylate (3A)", Syn. Comm. 21(7): 959–964 (1991).

*Primary Examiner*—Bernard Dentz
*Attorney, Agent, or Firm*—Daniel Reitenbach

[57] ABSTRACT

A process for the preparation of a substituted 2-benzo[b] thiophenecarboxylic acid compound or an alkali metal salt thereof, which comprises reacting a halobenzoyl derivative with mercaptoacetic acid in the presence of an alkali metal hydroxide and water. Substituted 2-benzo[b] thiophenecarboxylic acid compounds and alkali metal salts thereof are useful as intermediates for pharmaceuticals, agricultural chemicals, material preservatives, and the like.

23 Claims, No Drawings

PROCESS FOR SYNTHESIZING SUBSTITUTED 2-BENZO [B] THIOPHENECARBOXYLIC ACIDS AND SALTS THEREOF

FIELD OF THE INVENTION

This invention relates to a process for the preparation of 2-benzo[b]thiophenecarboxylic acid derivatives and alkali metal salts thereof.

BACKGROUND OF THE INVENTION

2-Benzo[b]thiophenecarboxylic acids and derivatives thereof are useful as intermediates in the manufacture of pharmaceuticals, agricultural chemicals, and in material preservation chemicals. See, e.g., European Patent 0 715 625.

Kolasa et al, Syn. Comm. 23(6): 743–8 (1993), describe an anhydrous process for the preparation of ethyl 2-benzo[b]thiophenecarboxylate by the reaction of 2-nitrobenzaldehyde and ethyl mercaptoglycolate in dimethylformamide (DMF) solvent and anhydrous potassium carbonate.

Zambias et al, Syn. Comm. 21(7): 959–964 (1991), describe a method for the preparation of methyl 2-benzo[b]thiophenecarboxylate which comprises: (1) reacting 2-chloro-5-nitrobenzaldehyde with methyl thioglycolate in methanol at 50–60° C. in the presence of sodium methoxide; and then (2) heating the resultant reaction mixture at reflux in the additional presence of sodium hydroxide.

U.S. Pat. No. 5,298,630 describes a two step process for the preparation of 2-benzo[b]thiophenecarboxylic acid: (1) reacting a 2-halobenzaldehyde with an alkyl mercaptan in the presence of alkali at reflux temperature, preferably using a phase transfer catalyst, to produce a 2-alkylthiobenzaldehyde intermediate; and then (2) treating this intermediate with a 2-haloacetic acid at 110° C. to produce 2-benzo[b]thiophenecarboxylic acid and an alkyl halide by-product.

Japanese Kokai Patent Application JP-05194484 describes a method for the preparation of benzo[b]thiophene-2-carboxylic acid which comprises: (1) reacting a 2-chlorobenzaldehyde with a dialkali salt of 2-mercaptoacetic acid, in an aprotic polar solvent, to produce a 2-[(2-formylphenyl)thio]acetate alkali metal salt intermediate; and then (2) cyclizing the intermediate in the presence of a base, to produce the benzo[b]-thiophene-2-carboxylic acid after neutralization. This method is conducted anhydrously and requires two separate organic solvents.

It is the purpose of this invention to provide a novel process for the preparation of 2-benzo[b]thiophenecarboxylic acid derivatives in an aqueous medium and without an organic solvent.

SUMMARY OF THE INVENTION

This invention relates to a process for the preparation of a 2-benzo[b]thiophenecarboxylic acid compound of the formula

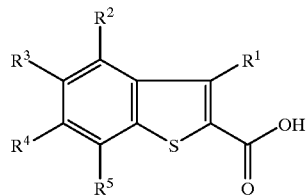

(I)

wherein, $R^1$ is H or $C_1$–$C_4$ alkyl; and $R^2$, $R^3$, $R^4$ and $R^5$ are, independently, hydrogen, halogen, $C_1$–$C_4$ alkyl, $C_1$–$C_4$ alkoxy, $C_1$–$C_4$ alkylthio, trifluoromethyl, acetyl, benzoyl, nitro, cyano or aryl, which process comprises (a) reacting a halobenzoyl compound of the formula

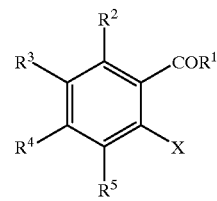

wherein X is halogen, and $R^1$, $R^2$, $R^3$, $R^4$ and $R^5$ are as described above, with mercaptoacetic acid in the presence of an alkali metal hydroxide and water, at a temperature of between about 100° C. and about 150° C. and at a pressure of between about 5 psi and about 50 psi, to produce a 2-benzo[b]thiophenecarboxylic acid alkali metal salt; and (b) neutralizing the 2-benzo[b]thiophenecarboxylic acid alkali metal salt, to produce the 2-benzo[b]thiophenecarboxylic acid compound.

The 2-benzo[b]thiophenecarboxylic acid alkali metal salt can be neutralized to the free carboxylic acid by acidification with a suitable mineral acid.

This invention also relates to a process for the preparation of a 2-benzo[b]thiophenecarboxylic acid alkali metal salt of the formula

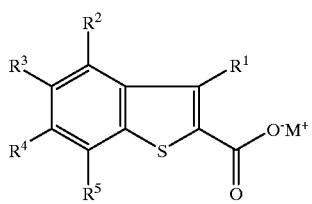

(IA)

wherein $R^1$, $R^2$, $R^3$, $R^4$ and $R^5$ are as described above, and M is an alkali metal, which process comprises (a) reacting a halobenzoyl compound of the formula

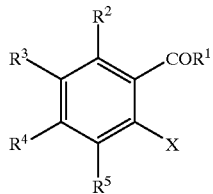

wherein X is halogen, and $R^1$, $R^2$, $R^3$, $R^4$ and $R^5$ are as described above, with mercaptoacetic acid in the presence of an alkali metal hydroxide and water, at a temperature of between about 100° C. and about 150° C. and at a pressure of between about 5 psi and about 50 psi, to produce the 2-benzo[b]thiophenecarboxylic acid alkali metal salt.

DESCRIPTION OF THE INVENTION

Halobenzoyl compounds of the formula

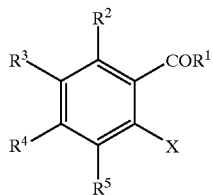

wherein X, $R^1$, $R^2$, $R^3$, $R^4$ and $R^5$ are as described above, are known. Certain of these halobenzoyl compounds, e.g., 5,6-dichlorobenzaldehyde and 2-chloro-5-(trifluoromethyl) benzaldehyde, are commercially available, e.g., from Aldrich Chemical Company, Inc.

Mercaptoacetic acid is also known as thioglycolic acid.

Useful alkali metal hydroxides can include sodium hydroxide, potassium hydroxide, calcium hydroxide, magnesium hydroxide, and the like, preferably, calcium hydroxide and magnesium hydroxide.

The term "phase transfer catalyst" means a catalyst which facilitates the solubility of water-soluble organic compounds in water-insoluble organic liquids. Preferred phase transfer catalysts include tetrabutylammonium bromide (TBAB) and benzyltrimethylammonium chloride.

"Neutralizing the 2-benzo[b]thiophenecarboxylic acid alkali metal salt" means lowering the pH of its environment, preferably to about pH 7 or lower. Such neutralization liberates and precipitates the free acid. One method to determine an effective amount of mineral acid useful in neutralizing the 2-benzo[b]thiophenecarboxylic acid alkali metal salt, is to add the mineral acid to the aqueous solution of the 2-benzo[b]thiophenecarboxylic acid alkali metal salt until no more precipitation occurs. The precipitate is the 2-benzo[b]thiophenecarboxylic acid. Useful mineral acids can include hydrochloric acid, sulfuric acid, and the like.

Preferably, this invention relates to a process for the preparation of a 2-benzo[b]thiophenecarboxylic acid compound of the formula

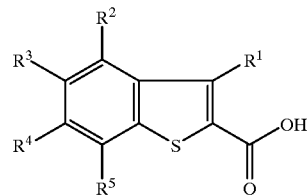

(I)

wherein $R^1$ is H or $C_1$–$C_4$ alkyl; and
$R^2$, $R^3$, $R^4$ and $R^5$ are, independently, hydrogen, halogen, $C_1$–$C_4$ alkyl, $C_1$–$C_4$ alkoxy, $C_1$–$C_4$ alkylthio, trifluoromethyl, acetyl, benzoyl, nitro, cyano or aryl, which process comprises (a) reacting a halobenzoyl compound of the formula

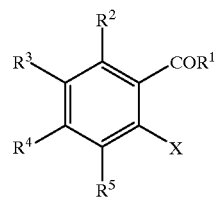

wherein X is halogen, and $R^1$, $R^2$, $R^3$, $R^4$ and $R^5$ are as described above, with mercaptoacetic acid, in the presence of a 10–15% (w/w) aqueous alkali metal hydroxide solution, and, optionally, in the presence of a phase transfer catalyst, at a temperature of between about 114–140° C., more preferably, between 115–125° C., and a pressure of between about 10 and 30 psi, more preferably, between about 15 to 25 psi, for about 1 to about 5 hours, more preferably, about 3 hours, to produce a 2-benzo[b]thiophenecarboxylic acid alkali metal salt; and (b) neutralizing the 2-benzo[b]thiophenecarboxylic acid alkali metal salt with a mineral acid, preferably, hydrochloric acid, to produce the 2-benzo[b]thiophenecarboxylic acid compound.

The amounts of halobenzoyl compound, alkali metal hydroxide, mercaptoacetic acid, and the optional phase transfer catalyst, can vary depending upon the choice of reaction components and conditions. Preferably, the ratio (w/w) of the halobenzoyl compound to the mercaptoacetic acid is between about 3:1 and about 1:1, more preferably, between about 2:1 and about 1:1. The ratio (w/w) of the halobenzoyl compound to the alkali metal hydroxide is preferably between about 1:3 and about 3:1, more preferably, between about 2:1 and about 1:1. The ratio (w/w) of the halobenzoyl compound to the phase transfer catalyst is preferably between about 5:1 and about 50:1, more preferably, between about 20:1 and about 40:1.

The concentration of the halobenzoyl compound in the reaction mixture can vary depending upon the choice of reaction components and conditions. Preferably, the concentration (w/v) of the halobenzoyl is from about 5% to about 25%, more preferably, from about 10% to about 15%.

Preferably, $R^1$ is hydrogen, methyl or ethyl; $R^2$, $R^3$, $R^4$ and $R^5$ are, independently, hydrogen, halogen, $C_1$–$C_4$ alkyl, or trifluoromethyl; and X is chlorine.

The following examples are presented to illustrate the present invention.

EXAMPLES

Example 1 Preparation of 2-benzo[b]thiophenecarboxylic acid (A) Potassium hydroxide pellets (12.5 g) were dissolved in water (105 ml) in a glass pressure bottle cooled in an ice bath. Then under a blanket of nitrogen, 2-mercaptoacetic acid (6.6 ml) was added to the glass pressure bottle, to produce a reaction mixture. A slight exotherm was observed. 2-Chlorobenzaldehyde (10.6 g, 0.075 mol) and tetrabutylammonium bromide (TBAB) (2 mole %) (0.5 g) were then added to the reaction mixture. Throughout, the reaction mixture was stirred magnetically. The glass pressure bottle was then capped and sealed tight using a cap equipped with a pressure gauge. The sealed pressure bottle was then emersed in an oil bath and heated behind a protective shield. Heating was gradual, and within 2.5 hours the internal bottle temperature had reached 245° F. (118.3° C.) and a pressure of 19 psi was observed. Heating was maintained at this temperature and pressure for another 3 hours. The reaction mixture was then allowed to cool to ambient temperature overnight. A fine, pale yellow precipitate of the potassium salt of 2-benzo[b]thiophenecarboxylic acid had deposited. This precipitate was collected on a filter, washed with ether, suspended in water and acidified with hydrochloric acid. The resultant acidified precipitate was then collected on a filter, washed with water and dried, to produce a first crop of 2-benzo[b]thiophenecarboxylic acid. The resultant filtrate was then acidified with hydrochloric acid. The precipitate obtained from this acidification was then collected on a filter, washed with water and dried, to produce a second crop of 2-benzo[b]thiophenecarboxylic acid. The combined crops gave 11.7 g of 2-benzo[b]thiophenecarboxylic acid (87.6% yield). NMR confirmed the structure as that of 2-benzo[b]thiophenecarboxylic acid.

(B) A reaction mixture of water (2.05 l), potassium hydroxide (247 g), 2-mercaptoacetic acid (135.0 ml), 2-chlorobenzaldehyde (209.1 g, 99%) and TBAB (5 g) was produced in a 1 US gallon autoclave under nitrogen and heated. A temperature of 124° C. was attained in 3 hours and held for another 4 hours before dropping the heating jacket. The reaction mixture was then allowed to cool to ambient temperature overnight. A fine, pale yellow precipitate of the potassium salt of 2-benzo[b]thiophenecarboxylic acid had deposited. This precipitate was collected on a filter, washed with toluene, suspended in water and acidified. The resultant acidified precipitate was then collected on a filter, washed with water and dried, to produce a first crop of 2-benzo[b]thiophenecarboxylic acid. The resultant filtrate was then acidified with hydrochloric acid. The precipitate obtained from this acidification was then collected on a filter, washed with water and dried, to produce a second crop of 2-benzo[b]thiophenecarboxylic acid. The combined crops gave 245.1 g of 2-benzo[b]thiophenecarboxylic acid (92% yield).

(C) The procedure described above in (B) was repeated except no TBAB was used. 241.1 g of 2-benzo[b]thiophenecarboxylic acid was isolated (90.3% yield).

(D) A reaction mixture of water (644 lbs), potassium hydroxide (176.5 lbs), 2-mercaptoacetic acid (69.5 lbs), 2-chlorobenzaldehyde (80 lbs), and TBAB (2 lbs) was prepared in a 150 US gallon glass lined reactor. The reactor was heated to 124–128° C. at 23–24.3 psi and held for 5 hours. The reaction mixture was then allowed to cool to ambient temperature overnight. A fine, pale yellow precipitate of the potassium salt of 2-benzo[b]thiophenecarboxylic acid had deposited. This precipitate was collected on a filter, washed with toluene, suspended in water and acidified with hydrochloric acid. The resultant acidified precipitate was then collected on a filter, washed with water and dried, to produce a first crop of 2-benzo[b]thiophenecarboxylic acid. The resultant filtrate was then acidified with hydrochloric acid. The precipitate obtained from this acidification was then collected on a filter, washed with water and dried, to produce a second crop of 2-benzo[b]thiophenecarboxylic acid. The combined crops gave 84.9 lbs of 2-benzo[b]thiophenecarboxylic acid (83.8% yield).

Example 2 A. Preparation of 7-chloro-2-benzo[b]thiophenecarboxylic acid

In a glass pressure bottle, 2,3-dichlorobenzaldehyde (17.5 g, 0.1 mol) was added to a solution of thioglycolic acid (7.0 ml) in potassium hydroxide (12.5 g) and water (100 ml). The bottle was then sealed and heated in a hot oil bath to 125±5° C. for 1.25 hours. The bottle was then removed from the hot oil bath and cooled. A pale yellow precipitate was obtained in the bottle. At ambient temperature, the bottle was opened and sufficient water was added to dissolve the precipitate. The resultant aqueous material was washed with ether and then acidified with hydrochloric acid to produce a pale yellow solid. The pale yellow solid was collected on a filter, washed with water and dried, to produce 17.2 g of 7-chloro-2-benzo[b]thiophenecarboxylic acid (83.8% yield, mp 262–265° C.)

B. Preparation of 7-chloro-2-benzo[b]thiophenecarboxylic acid chloride 16.6 g of the 7-chloro-2-benzo[b]thiophenecarboxylic acid prepared in A above was added to thionyl chloride (48 ml) and toluene (10 ml) and refluxed for 4 hours. Excess thionyl chloride was then removed and the resultant residue was treated with toluene (20 ml). The toluene was then removed under reduced pressure to produce 17.8 g of 7-chloro-2-benzo[b]thiophenecarboxylic acid chloride as a reddish solid.

C. Preparation of S-ethyl 7-chloro-2-benzo[b]thiophenecarbothioate 17.8 g of the 7-chloro-2-benzo[b]thiophenecarboxylic acid chloride prepared in B above, was dissolved in toluene (100 ml), treated with ethanethiol (6.2 ml) followed by dropwise addition of a solution of triethylamine (11.2 ml) in toluene (6 ml) at 15° C., with vigorous stirring, to produce a reaction mixture. The reaction mixture was allowed to come to ambient temperature and then stirred overnight. Water (60 ml) was then added to the reaction mixture and the resultant organic layer was separated. The organic layer was washed with water (50 ml), then with hydrochloric acid (50 ml, 1N), dried ($MgSO_4$), filtered and evaporated, to produce 18,8 g of S-ethyl 7-chloro-2-benzo[b]thiophenecarbothioate.

D. Preparation of ethyl 7-chloro-2-benzo[b]thiophenecarbodithioate 17 g of the ethyl 7-chloro-2-benzo[b]thiophenecarbothioate prepared in C above, in toluene (170 ml) was treated with phosphorus pentasulphide (22.1 g) to produce a reaction mixture. The reaction mixture was refluxed for 4 hours, at which time thin layer chromatography ("TLC") (40:60, methylene chloride:hexane) showed no S-ester present. The reaction mixture was then cooled and filtered. The filtrate was washed with water and stirred with saturated aqueous sodium bicarbonate (50 ml) until all gassing had ceased. The resultant organic layer was separated, washed with water, dried (MgSO$_4$), filtered and evaporated to produce 17.8 g of a red solid. The red solid was then recrystallized from methanol to produce 14 g of ethyl 7-chloro-2-benzo[b]thiophenecarbodithioate. NMR confirmed the structure as that of ethyl 7-chloro-2-benzo[b]thiophenecarbodithioate.

Example 3 A. Preparation of 5-fluoro-2-benzo[b]thiophenecarboxylic acid

In a glass pressure bottle, 2,5-difluorobenzaldehyde (11 ml, 0.1 mol) was added to a solution of 2-mercaptoacetic acid (9 ml) in potassium hydroxide (16.5 g) and water (155 ml). The bottle was then sealed and heated in a hot oil bath to 125±5° C. for 1.25 hours. The bottle was then removed from the hot oil bath and cooled. A pale yellow precipitate was obtained in the bottle. At ambient temperature, the bottle was opened and sufficient water was added to dissolve the precipitate. The resultant aqueous material was washed with ether and then acidified with hydrochloric acid to produce a pale yellow solid. The pale yellow solid was collected on a filter, washed with water and dried, to produce 15.5 g of 5-fluoro-2-benzo-[b]thiophenecarboxylic acid (80.1% yield, mp>300° C.).

B. Preparation of ethyl 4-fluoro-2-benzo[b]thiophenecarbodithioate

The 5-fluoro-2-benzo[b]thiophenecarboxylic acid prepared above in A was converted to ethyl 5-fluoro-2-benzo[b]thiophenecarbodithioate (mp 91–92° C.) using the procedures described above in Examples 2(B)–2(D). NMR confirmed the structure as that of ethyl 5-fluoro-2-benzo[b]thiophenecarbodithioate.

Example 4 A. Preparation of 5-(trifluoromethyl)-2-benzo[b]thiophenecarboxylic acid In a glass pressure bottle, 2-chloro-5-(trifluoromethyl)benzaldehyde (10 g, 0.048 mol) and TBAB (0.2 g) was added to a solution of 2-mercaptoacetic acid (4.7 ml) in potassium hydroxide (8.4 g) and water (85 ml). The bottle was then sealed and heated in a hot oil bath to 140° C. for 45 minutes, to produce a reaction mixture. Once the reaction mixture became homogenous, the bottle was then removed from the hot oil bath and cooled. At ambient temperature, the bottle opened and contents made homogenous by adding water. The resultant aqueous material was washed with ether and then acidified with hydrochloric acid to produce a pale yellow solid. The pale yellow solid was collected on a filter, washed with water and dried, to produce 11.1 g of 4-(trifluoromethyl)-2-benzo[b]thiophenecarboxylic acid (94% yield, mp 178–179° C.).

B. Preparation of ethyl 5-(trifluoromethyl)-2-benzo[b]thiophenecarbodithioate

The 5-(trifluoromethyl)-2-benzo[b]thiophenecarboxylic acid prepared above in A was converted to ethyl 5-(trifluoromethyl)-2-benzo[b]thiophenecarbodithioate (mp 67–68° C.) using the procedures described above in Examples 2(B)–2(D). NMR confirmed the structure as that of ethyl 5-(trifluoromethyl)-2-benzo[b]thiophenecarbodithioate.

Example 5 Preparation of 3-methyl-2-benzo[b]thiophenecarboxylic acid

Potassium hydroxide (12.5 g) was dissolved in water (105 ml) in a glass pressure bottle cooled in an ice bath. Then under a blanket of nitrogen, thioglycolic acid (7 ml) was added to the glass pressure bottle, to produce a reaction mixture. 2'-chloroacetophenone (12 g, 97%, 0.075 mol) and TBAB (0.5 g) were then added to the reaction mixture. The glass pressure bottle was then sealed and heated to 253° F. for 6 hours at 18 psi. The reaction was shut down and left overnight. Heating was then resumed at 270° F. at 30 psi for six hours and then cooled to ambient temperature. After the bottle was opened, the reaction mixture was washed with ether to remove organics, and acidified with hydrochloric acid to give 3.9 g of crude 3-methyl 2-benzo[b]thiophenecarboxylic acid (27% yield, mp>200° C.).

Example 6 A. Preparation of 4-chloro-2-benzo[b]thiophenecarboxylic acid

In a glass pressure bottle, 2,6-dichlorobenzaldehyde (13.5 g, 0.075 mol) and TBAB (0.4 g) was added to a solution of 2-mercaptoacetic acid (7 ml) in potassium hydroxide (12.5 g) and water (100 ml). The bottle was then sealed and heated in a hot oil bath at 255° F. and 20 psi for 1 hour The bottle was then removed from the hot oil bath and cooled. A pale yellow precipitate was obtained in the bottle. At ambient temperature, the bottle was opened and sufficient water was added to dissolve the precipitate. The resultant aqueous material was washed with ether and then acidified with hydrochloric acid to produce a pale yellow solid. The pale yellow solid was collected on a filter, washed with water and dried, to produce 18.1 g of 4-chloro-2-benzo[b]thiophenecarboxylic acid (85.2% yield, mp 227–231° C.).

B. Preparation of ethyl 4-chloro-2-benzo[b]thiophenecarbodithioate

The 4-chloro-2-benzo[b]thiophenecarboxylic acid prepared above in A was converted to ethyl 4-chloro-2-benzo[b]thiophenecarbodithioate using the procedures described above in Examples 2(A)–2(B). NMR confirmed the structure as that of ethyl 4-chloro-2-benzo[b]thiophenecarbodithioate.

What is claimed is:

1. A process for the preparation of a 2-benzo-[b]thiophenecarboxylic acid compound of the formula

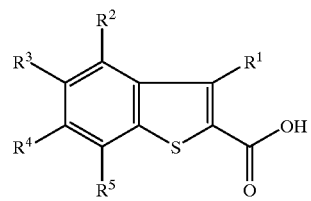

(I)

wherein,
  $R^1$ is H or $C_1$–$C_4$ alkyl; and
  $R^2$, $R^3$, $R^4$ and $R^5$ are, independently, hydrogen, chlorine, fluorine, $C_1$–$C_4$ alkyl, $C_1$–$C_4$ alkoxy, $C_1$–$C_4$ alkylthio, trifluoromethyl, acetyl, benzoyl, cyano or aryl, which process comprises (a) reacting a halobenzoyl compound of the formula

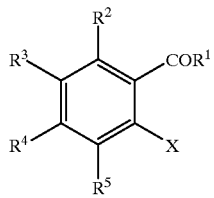

wherein X is halogen, and $R^1$, $R^2$, $R^3$, $R^4$ and $R^5$ are as described above, with mercaptoacetic acid in the presence of an alkali metal hydroxide and water, at a temperature of between about 100° C. and 150° C., and at a pressure of between about 5 and 50 psi, to produce a 2-benzo[b]thiophenecarboxylic acid alkali metal salt; and (b) neutralizing the 2-benzo[b]thiophenecarboxylic acid alkali metal salt, to produce the 2-benzo[b]thiophenecarboxylic acid compound.

2. A process as recited in claim 1 wherein $R^1$ is hydrogen, methyl or ethyl; $R^2$, $R^3$, $R^4$ and $R^5$ are, independently, hydrogen, halogen, $C_1$–$C_4$ alkyl, or trifluoromethyl; and X is chlorine.

3. A process as recited in claim 1 wherein the alkali metal hydroxide is selected from the group consisting of sodium hydroxide and potassium hydroxide.

4. A process as recited in claim 1 wherein the halobenzoyl compound is reacted with the mercaptoacetic acid at a temperature of between about 110° C. and about 140° C.

5. A process as recited in claim 4 wherein the halobenzoyl compound is reacted with the mercaptoacetic acid at a temperature of between about 115° C. and about 125° C.

6. A process as recited in claim 1 wherein the halobenzoyl compound is reacted with the mercaptoacetic acid at a pressure of between about 10 and about 30 psi.

7. A process as recited in claim 6 wherein the halobenzoyl compound is reacted with the mercaptoacetic acid at a pressure of between about 15 to about 25 psi.

8. A process as recited in claim 1 wherein the halobenzoyl compound is reacted with the mercaptoacetic acid for about 1 to about 5 hours.

9. A process as recited in claim 1 wherein the halobenzoyl compound is reacted with the mercaptoacetic acid in the presence of a phase transfer catalyst.

10. A process as recited in claim 9 wherein the phase transfer catalyst is tetrabutylammonium bromide (TBAB) or benzyltrimethylammonium chloride.

11. A process as recited in claim 1 wherein the 2-benzo[b]thiophenecarboxylic acid alkali metal salt is neutralized with a mineral acid.

12. A process as recited in claim 11 wherein the mineral acid is hydrochloric acid or sulfuric acid.

13. A process for the preparation of a 2-benzo-[b]thiophenecarboxylic acid alkali metal salt of the formula

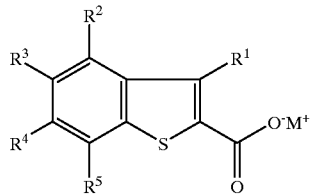

(IA)

wherein,
$R^1$ is H or $C_1$–$C_4$ alkyl;
$R^2$, $R^3$, $R^4$ and $R^5$ are, independently, hydrogen, chlorine, fluorine, $C_1$–$C_4$ alkyl, $C_1$–$C_4$ alkoxy, $C_1$–$C_4$ alkylthio, trifluoromethyl, acetyl, benzoyl, cyano or aryl; and
M is an alkali metal,
which process comprises
(a) reacting a halobenzoyl compound of the formula

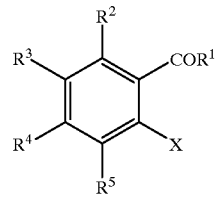

wherein X is halogen, and $R^1$, $R^2$, $R^3$, $R^4$ and $R^5$ arc as described above,
with mercaptoacetic acid in the presence of an alkali metal hydroxide and water, at a temperature of between about 100° C. and 150° C., and at a pressure of between about 5 and 50 psi,
to produce the 2-benzo[b]thiophenecarboxylic acid alkali metal salt.

14. A process as recited in claim 13 wherein $R^1$ is hydrogen, methyl or ethyl; $R^2$, $R^3$, $R^4$ and $R^5$ are, independently, hydrogen, halogen, $C_1$–$C_4$ alkyl, or trifluoromethyl; and X is chlorine.

15. A process as recited in claim 13 wherein the alkali metal hydroxide is selected from the group consisting of sodium hydroxide and potassium hydroxide; and M is sodium or potassium, respectively.

16. A process as recited in claim 13 wherein the halobenzoyl compound is reacted with the mercaptoacetic acid at a temperature of between about 114° C. and about 140° C.

17. A process as recited in claim 16 wherein the halobenzoyl compound is reacted with the mercaptoacetic acid at a temperature of between about 115° C. and about 125° C.

18. A process as recited in claim 13 wherein the halobenzoyl compound is reacted with the mercaptoacetic acid at a pressure of between about 10 and about 30 psi.

19. A process as recited in claim 18 wherein the halobenzoyl compound is reacted with the mercaptoacetic acid at a pressure of between about 15 to about 25 psi.

20. A process as recited in claim 13 wherein the halobenzoyl compound is reacted with the mercaptoacetic acid for about 1 to about 5 hours.

21. A process as recited in claim 13 wherein the halobenzoyl compound is reacted with the mercaptoacetic acid in the presence of a phase transfer catalyst.

22. A process as recited in claim 21 wherein the phase transfer catalyst is tetrabutylammonium bromide (TBAB) or benzyltrimethylammonium chloride.

23. A process for the preparation of a 2-benzo-[b]thiophenecarboxylic acid compound of the formula

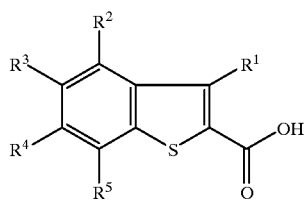

(I)

wherein,
R$^1$ is H or C$_1$–C$_4$ alkyl; and
R$^2$, R$^3$, R$^4$ and R$^5$ are, independently, hydrogen, chlorine, fluorine, C$_1$–C$_4$ alkyl, C$_1$–C$_4$ alkoxy, C$_1$–C$_4$ alkylthio, trifluoromethyl, acetyl, benzoyl, cyano or aryl, which process comprises neutralizing a 2-benzo[b]thiophenecarboxylic acid alkali metal salt produced by the process as recited in claim 13.

* * * * *